United States Patent [19]

Muramatsu et al.

[11] Patent Number: 5,334,516
[45] Date of Patent: Aug. 2, 1994

[54] PRODUCTION METHOD OF BRANCHED FRUCTOOLIGOSACCHARIDES

[75] Inventors: Masayoshi Muramatsu, Fuji; Teruo Nakakuki, Mishima; Seishiro Kainuma, Shimizu; Taizo Miwa, Sagamihara, all of Japan

[73] Assignee: Nihon Shokuhin Kako Co., Ltd., Tokyo, Japan

[21] Appl. No.: 234,684

[22] Filed: Aug. 22, 1988

[30] Foreign Application Priority Data

Sep. 4, 1987 [JP] Japan ............................... 62-221347

[51] Int. Cl.$^5$ ............................................. C12P 19/04
[52] U.S. Cl. ................................. 435/101; 435/254.1; 435/913; 435/200
[58] Field of Search ................ 435/101, 99, 162, 254, 435/911, 196, 131, 254.1, 200, 913

[56] References Cited

PUBLICATIONS

Teruo, Nakakuki et al. "Research on the Production of Fructooligosaccharides," Mar. 10, 1987, p. 657 of Abstract of the Annual Meeting, Showa 62 (1987) Tokyo.
Chemical Abstracts, Murasmatsu et al., "Structures of Some Fructooligosaccharides Produced From Sucrose by Mycelia of *Aspergillus sydowi*," Aug. 15, 1988, p. 363, #51364(y), vol. 109.
Chemical Abstracts, Kawai ·et al., "Polyfructan and Oligofructans Synthesized From Sucrose by Conidia of *Aspergillus sydoiwi*" , Dec. 24, 1973, p. 132, #144075(g), vol. 79.
Chemical Abstracts, Nakakuki et al., "Manufacture of Oliga-and Polyfructans from Sucrose by Aspergillus," Jan. 5, 1987, p. 374, #3868(g), vol. 106.
Muramatsu et al., "Structures of Some Fructooligosaccharides Produced from Sucrose by Mycelia of *Aspergillus sydowi* IAM 2544", Agricultural and Biological Chemistry, vol. 52, No. 5, May 1988, pp. 1303–1304.
Patent Abstracts of Japan, vol. 11, (No. 132), Apr. 1987, Abstract 61-268190 to Meiji Seika Kaisha Ltd.
Patent Abstracts of Japan, vol. 8, (No. 41), Feb. 1984, Abstract 58-201980 to Meiji Seika Kaisha Ltd.
Shiomi et al., "A Novel Pentasaccharide in the Roots of Asparagus", Agricultural and Biological Chemistry, vol. 43, (No. 6) 1979 pp. 1375–1377.
Teruo Nakakuki, Masayoshi Muramatsu, Seishrio Kainuma and Taizo Miwa, "Research on the Production of a Fructooligosaccharide", Mar. 10, 1987, p. 657 of Abstract of the Annual Meeting, Showa 62 (1987) Tokyo (Japanese language).
Nicholas Kopeloff, Lillian Kopeloff and C. J. Welcome, "Formation of the Gum, Levan, by Mold Spores", Apr. 15, 1920, pp. 171–187 of J. Biol. Chem., 43 (1920).
Gneshiro Kawai, Hajime Taniguchi and Michinori Nakamura, "Polyfructan and Oligofructans Synthesized from Sucrose by Conidia of *Asperfillus sydowi* IAM 2544", pp. 2111–2119, 1973 of Agr. Biol. Chem., vol. 37, No. 9.

*Primary Examiner*—Douglas W. Robinson
*Attorney, Agent, or Firm*—Beveridge, DeGrandi & Weilacher

[57] ABSTRACT

This invention relates to a method for production on an industrial scale of the branched fructooligosaccharide indicated by the general structural formula below using microorganisms or an enzyme produced by microorganisms which belong to the genus Aspergillus, wherein in the formula above, $m = 0\text{-}10$, $n = 0\text{-}8$ and $m + n = 3\text{-}10$.

12 Claims, No Drawings

PRODUCTION METHOD OF BRANCHED FRUCTOOLIGOSACCHARIDES

BACKGROUND OF THE INVENTION

This invention relates to a method for the production of branched fructooligosaccharides which have a specific structure utilizing microorganisms or an enzyme which is produced by microorganisms belonging to the genus Aspergillus using sucrose as raw material.

The physiological activity possessed by fructooligosaccharides has recently become of major interest ["KagaKu to Seibutsu" (Chemistry and Biology), Vol. 21, p. 291]. For example, fructooligosaccharides are difficult to digest and are selectively utilized by useful intestinal flora, Lactobacillus bifidus in particular, thereby promoting proliferation of these organisms and improving laxation and the like. In addition, when broken down by Lactobacillus bifidus, organic acids are produced. These have been recognized to have the effect of reducing cholesterol levels in the body.

Fructooligosaccharides are formed as a result of a fructose transferase (fructosyl transferase) acting on sucrose. Microorganisms that are known to form fructose transferases include yeast, Aspergillus niger, Aureobasidium pullulans, etc. In addition, as has been previously shown by the inventors, fructooligosaccharides can also be effectively produced using fructose transferase produced by Aspergillus sydowi [see TOKYO-KOKAI-KOHO (18-month Publication of Unexamined Patent Application) SHOWA 61(1986)-187797 (hereinafter referred to as TOKKAISHO 61-187797)].

However, these fructose transferases acted on sucrose and either formed fructooligosaccharides with a structure in which several fructose are linked by $\beta$-1,2 bonds to the fructose residue of sucrose, or formed high molecular weight polyfructan composed of the same linkages. Examples of sugars obtained using the fructose transferase produced by microorganisms such as those indicated above and having structures other than these have thus far not been reported.

Conversely, it is known that fructooligosaccharides are produced by various plants ("Kagaku to Seibutsu", Vol. 18, p. 674). It has been reported that non-reducing fructose polymers having a degree of polymerization of 3-15 exist in the storage roots of asparagus in particular, and their structures have been elucidated [N. Shiomi, J. Yamada & M. Izawa, Agric. Biol. Chem., 40, 567 (1976), 43, 1375 (1979), 43, 2233 (1979)]. The fructooligosaccharides found in the storage roots of asparagus have a structure in which fructose is linked at both the glucose residue and fructose residue of sucrose resulting in the structure having a branching form. Fructooligosaccharides having these structures were not found in fructooligosaccharides that are formed using microorganisms.

The purpose of this invention is to provide a method for the production of branched fructooligosaccharides so that naturally-occurring branched fructooligosaccharides, which have heretofore been known only to exist in higher plants, are able to be industrially produced using enzymes of microorganisms.

As was previously stated, although the inventors had shown that fructooligosaccharides such as 1-ketose and nystose, in which fructose is linked by $\beta$-1,2 bonds at the fructose residue of sucrose, can be obtained utilizing the mycelia of Aspergillus sydowi, as a result of following research, it was found that branched fructooligosaccharides in which fructose is linked to both the glucose residues and fructose residues of sucrose can be obtained simultaneously with the above fructooligosaccharides under the same reaction conditions, and this has lead to the completion of this invention.

SUMMARY OF THE INVENTION

In summary, this invention is a method for the production of branched fructooligosaccharides which is characterized by its forming the branched fructooligosaccharide indicated by the general structural formula (A) shown below through the treatment of sucrose using the mycelia, or the enzyme prepared from the mycelia, of microorganisms belonging to the genus Aspergillus which have the ability to produce fructose transferase.

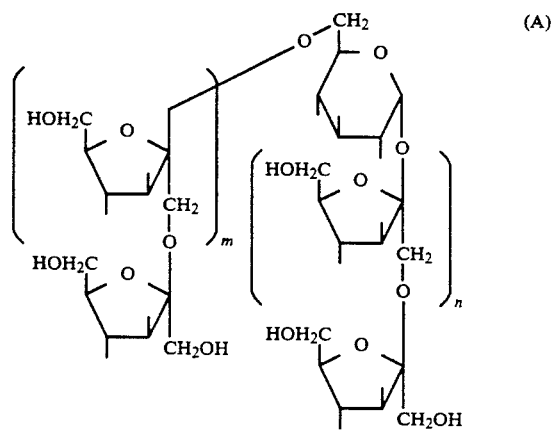

(In the formula above, m=0–10, n=0–8 and m+n=3–10).

Although any member of the genus Aspergillus which has the ability to produce fructose transferase would be satisfactory as the microorganism used in this invention, Aspergillus sydowi is particularly preferable. Examples of stock types of Aspergillus sydowi used include IAM 2544, IAM 2514, IAM 2078 and IAM 2009 (all of which are Type Culture Collection Numbers of Institute of Applied Microbiology, University of Tokyo).

According to this invention, it is possible to produce on an industrial scale branched fructooligosaccharides, which had heretofore only existed in higher plants such as the storage roots of asparagus, using the mycelia of microorganisms or the enzyme prepared from such mycelia. In addition, since the branched fructooligosaccharides that are obtained have a structure that is identical to the naturally-occurring branched fructooligosaccharides mentioned above, they have a high level of safety when added to food products. Further, these branched fructooligosaccharides are expected to demonstrate various effects in terms of their physiological activity, including the promotion of proliferation of Lactobacillus bifidus in the intestines of humans, thereby improving laxation.

DESCRIPTION OF THE PREFERRED EMBODIMENTS

Although either a solid or liquid medium is satisfactory as the medium for Aspergillus sydowi, the microorganism used in this invention, in the case of a liquid medium, a medium which contains the following components in particular would be optimal.

| Glucose | 10% (W/V) |
|---|---|
| Corn Steep Liquor | 2% |
| MgSO$_4$.7H$_2$O | 0.1% |
| KH$_2$PO$_4$ | 0.2% |
| pH = 6.0 | |

*Aspergillus sydowi* is inoculated into the medium that is described above and incubated under aerobic conditions by, for example, a shake culture using a rotary shaker, etc., or an agitation aeration culture using a jar fermentor, etc. An incubation temperature of approximately 30° C. is suitable.

When the organism is incubated for several days under these conditions, large numbers of mycelia of *Aspergillus sydowi* will be formed and incubation is concluded at this point. The mycelia are then collected by means of centrifugation and filtration. After washing with physiological saline, the mycelia are preserved using lyophilization. Furthermore, in the case of using a microorganism that belongs to the genus Aspergillus other than *Aspergillus sydowi*, the mycelia of that microorganism can be obtained using a similar method to that described above.

In this invention, branched fructooligosaccharides are produced from the treatment of sucrose using the mycelia of, or enzymes prepared from the mycelia of, a microorganism which has the ability to produce fructose transferase and belongs to the genus Aspergillus, that was obtained using the method described above.

In the case of using the mycelia, although they can be used as is, it is also possible to use mycelia that have been embedded and fixed using a sealer such as alginate, acrylamide gel, polyvinyl alcohol gel, photo cross-linking resin, carrageenan, chitosan or gelatin. Furthermore, the mycelia may also be treated with glutaraldehyde and the like in order to increase carrier strength. When using the mycelia as is, although it is necessary to treat by batch methods, when using mycelia that have been fixed, the mycelia can be charged on a column and continuously fed, allowing the reaction to be performed more efficiently than batch methods. In addition, when using enzyme that has been prepared from the mycelia, the mycelia are homogenated and the enzyme solution is extracted. This enzyme solution can then be used further purifying as necessary. In addition, the enzyme that is obtained can also be used immobilized onto a suitable carrier.

A pH of 5.0-7.0 is desirable and a pH of 5.5-6.5 is optimum for enzyme reaction conditions for the formation of branched fructooligosaccharides. A temperature of 30°-70° C. is desirable and a temperature of 40°-60° C. is even more desirable for the temperature conditions. The concentration of sucrose which is used for the raw material should be 30-80% (W/V) and 50-80% (W/V) would be even more preferable. In addition, the amount of fructose transferase that is used at that time should be 5 units or more per 1 g of solid sucrose. 1 unit here refers to the amount of enzyme which will transfer 1$\mu$ mol of fructose residue of sucrose to other sucrose or branched fructooligosaccharide in 1 minute while reacting at a pH of 6.0 and temperature of 60° C. in a substrate of 50% (W/V) sucrose solution.

After filtration, using for example, a membrane filter, deionization and decolorization of the reaction solution thus obtained, the solution can be concentrated and made into a syrup or made into a powder by spray drying. Furthermore, although the reaction solution contains a total of 30-50% (W/W) glucose, fructose and unreacted sucrose in addition to the fructooligosaccharides, these can be removed by either gel filtration using "Bio-Gel" (trademark; mfd. by Bio-Rad Co., Ltd.) or "Toyopearl HW40" (trademark; mfd. by Toyo Soda Kogyo Co., Ltd.), or by strongly acidic cation exchange resin column chromatography. It is also possible to obtain only branched fructooligosaccharide in high purity by separating the branched fructooligosaccharide from fructooligosaccharides such as 1-ketose and nystose using a method similar to that described above.

As was previously indicated in the general structural formula (A), the branched fructooligosaccharide obtained by this invention is an oligosaccharide with a degree of polymerization of 6 to 13 with 1-11 fructose linked to the glucose residue of sucrose and 1-9 fructose linked to the fructose residue. This branched fructooligosaccharide has a structure that is the same as that of naturally-occurring fructooligosaccharide contained in the storage roots of asparagus and has an extremely high degree of safety.

In the same manner as conventional fructooligosaccharides, the branched fructooligosaccharide obtained with this invention is expected to have the effect of acting to promote proliferation of *Lactobacillus bifidus* in the intestines of humans, thereby improving laxation. In addition, as it has not been observed to raise blood sugar levels in results of blood sugar loading tests, not being hydrolyzed by digestive enzymes in the body, applications on diabetic patients have also been considered. Furthermore, it has also been recognized to act in reducing cholesterol and neutral fat levels in the blood and liver.

Product forms of the branched fructooligosaccharide obtained with this invention include health food products in the form of a powder prepared by spray drying and a concentrated liquid, as well as use as an additive in other foods such as bread and biscuits.

EXAMPLE 1

100 ml of the liquid medium indicated below (pH 6.0) was placed in a Sakaguchi flask and *Aspergillus sydowi* IAM 2544 (Type Culture Collection Number of Institute of Applied Microbiology, University of Tokyo) was inoculated to the medium from a slant. This was then cultivated with reciprocal shaker for 5 days at 30° C. The organisms were collected by centrifuging the culture liquid and after washing several times with physiological saline, were lyophilized and submitted for testing.

| Glucose | 10% (W/V) |
|---|---|
| Corn Steep Liquor | 2% |
| MgSO$_4$.7H$_2$O | 0.1% |
| KH$_2$PO$_4$ | 0.2% |
| pH = 6.0 | |

Next, 5 units of the above mycelia were added per 1 g of solid sucrose to a 50% (W/V) sucrose solution (pH 6.0). While stirring at a temperature of 50° C., the solution was allowed to react for 2 days. Continuing, after removing the mycelia by filtration, each of the fructooligosaccharides was separated into fractions by carbon column chromatography. These fractions were then purified by gel filtration chromatography using "Toyopearl HW40S" trademark; mfd. by Toyo Soda Kogyo Co., Ltd.) to obtain fructooligosaccharides of high purity that possess a series of degrees of polymerization.

The series of fructooligosaccharides that were thus obtained were hydrolyzed using 0.1N hydrochloric acid or invertase to determine the respective molar ratios of glucose and fructose. The results of this are shown in Table 1.

TABLE 1

(Molar Ratios of Glucose and Fructose Following Hydrolysis of Formed Fructooligosaccharides)

|  | HCl Hydrolysis | | Invertase Hydrolysis | |
| --- | --- | --- | --- | --- |
|  | Glucose | Fructose | Glucose | Fructose |
| $GF_2$ | 1.0 | 2.0 | 1.0 | 2.2 |
| $GF_3$ | 1.0 | 3.0 | 1.0 | 3.0 |
| $GF_4$ | 1.0 | 3.9 | 1.0 | 3.9 |
| $GF_5$ | 1.0 | 5.2 | 1.0 | 5.0 |
| $GF_6$ | 1.0 | 6.3 | 1.0 | 6.3 |
| $GF_7$ | 1.0 | 7.6 | 1.0 | 7.2 |
| $GF_{8-12}$ | 1.0 | 8.6 | 1.0 | 8.2 |

(In the table, G refers to glucose and F refers to fructose.)

As is indicated in Table 1, the rise in the molar ratio of fructose accompanied the increase in the degree of polymerization regardless of which method of hydrolysis was employed. It has therefore been estimated that the structure of these fructooligosaccharides is such that fructose is linked to sucrose by $\beta$-fructofuranoside linkages.

Continuing, after methylation of these fructooligosaccharides by the known method of Hakomori, they were hydrolyzed with acid followed by reduction to glucitol acetates. These glucitol acetates were then analyzed by capillary gas chromatography. The results of this analysis are shown in Table 2.

Table 2

(Molar Ratios of Permethylated Glucitol Acetates)

|  | 2,3,4,6-Tetramethyl | 2,3,4-Trimethyl | 1,3,4,6-Tetramethyl | 3,4,6-Trimethyl | 3,4-Dimethyl |
| --- | --- | --- | --- | --- | --- |
| $GF_2$ | 1.0 | — | 1.0 | 0.9 | — |
| $GF_3$ | 1.0 | — | 1.0 | 2.2 | — |
| $GF_4$ | 1.0 | — | 1.0 | 3.3 | — |
| $GF_5$ | — | 1.0 | 1.9 | 3.2 | — |
| $GF_6$ | — | 1.0 | 1.7 | 4.0 | — |
| $GF_7$ | — | 1.0 | 2.0 | 6.6 | — |
| $GF_{8-12}$ | — | 1.0 | 1.8 | 6.9 | — |

As is indicated in Table 2, for the ratios of the peak areas of the permethylated sugars that were obtained, in contrast to the ratio of 2,3,4,6-TMG:1,3,4,6-TMG:3,4,6-TMG being 1:1:n−1 for $GF_{n=2-4}$, the ratio of 2,3,4-TMG:1,3,4,6-TMG: 3,4,6-TMG was 1:2:n−2 for $GF_{n=5-12}$. Based on this, it was clear that from among the fructooligosaccharides that were obtained, $GF_{n=2-4}$ were fructooligosaccharides that have the structure indicated by the general structural formula (B) below, and $GF_{n=5-12}$ were branched fructooligosaccharides that have the structure indicated by the general structural formula (A) which was shown earlier.

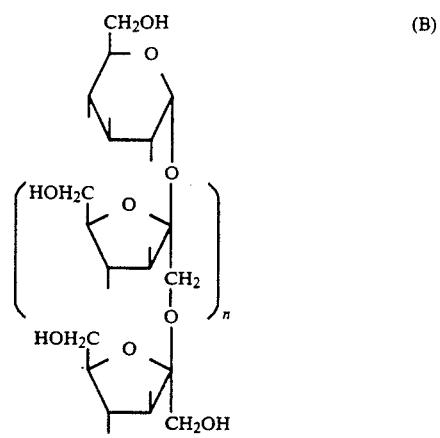

(In the formula above, n=1–3.)

As has been shown thus far, it is clear that the fructooligosaccharides with a degree of polymerization of 6 or greater that were obtained by allowing the mycelia of *Aspergillus sydowi* to act on sucrose are new branched fructooligosaccharides. Although these branched fructooligosaccharides are those found in the storage roots of asparagus, one of higher plants, these are the first to have been found as fructooligosaccharides that were produced by microorganisms.

EXAMPLE 2

In this example, a study was made of the effects of substrate concentration, added amount of mycelia and reaction temperature on the production of branched fructooligosaccharides using the lyophilized mycelia obtained in Example 1. The results of these studies are shown in Tables 3 through 5. As can be seen in the tables, a concentration of sucrose, the substrate, of 30% (W/V) or greater is preferable. In regard to the amount of mycelia enzyme that is added, a minimum of 5 units per 1 g of solid sucrose is preferable. In addition, it was also determined that a reaction temperature of 40°–60° C. yielded favorable results.

TABLE 3

(The Effect of Sucrose Concentration on Fructooligosaccharide Formation)

| Sucrose Conc. in Substrate Soln. (%) | Formed Sugar Composition (%) | | | | |
| --- | --- | --- | --- | --- | --- |
|  | $GF_{5-12}$ | $GF_{2-4}$ | Sucrose | Glucose | Fructose |
| 1 | — | 5.2 | 40.5 | 31.2 | 19.3 |
| 5 | 1.9 | 19.1 | 13.3 | 40.1 | 23.8 |
| 10 | 1.9 | 25.5 | 14.2 | 36.8 | 21.5 |
| 30 | 7.2 | 33.7 | 8.6 | 38.3 | 12.0 |
| 50 | 10.9 | 30.9 | 12.3 | 37.2 | 8.2 |

Reaction Conditions:

Mycelia having 5 units per 1 of solid sucrose of transferase activity were reacted with various concentrations of sucrose solutions (pH 6.0) at 50° C. for 88 hours.

$GF_{5-12}$:

Refers to branched fructooligosaccharides (with general structural formula A) having 4–11 fructose linked to sucrose.

$GF_{2-4}$:

Refers to fructooligosaccharides (with general structural formula B) having 1–3 fructose linked to sucrose.

TABLE 4

(The Effect of Amount of Added Mycelia Enzyme on Fructooligosaccharide Formation)

| Amt. of Mycelia Enzyme Added to Sucrose Soln. (unit/g) | Formed Sugar Composition (%) | | | | |
|---|---|---|---|---|---|
| | GF$_{5-12}$ | GF$_{2-4}$ | Sucrose | Glucose | Fructose |
| 1 | 2.0 | 33.7 | 38.1 | 22.4 | 3.7 |
| 2 | 4.5 | 40.9 | 20.0 | 30.0 | 4.2 |
| 5 | 10.9 | 30.9 | 12.2 | 37.2 | 8.2 |
| 10 | 11.0 | 30.0 | 12.1 | 38.0 | 8.5 |

Reaction Conditions:

Various concentrations of mycelia enzyme (fructose transferase) were reacted with 50% sucrose solution (pH 6.0) at 60° C. for 48 hours.

TABLE 5

(The Effect of Reaction Temperature on Fructo-oligosaccharide Formation)

| Reaction Temp. (°C.) | Formed Sugar Composition (%) | | | | |
|---|---|---|---|---|---|
| | GF$_{5-12}$ | GF$_{2-4}$ | Sucrose | Glucose | Fructose |
| 30 | 4.1 | 30.4 | 28.8 | 29.3 | 7.3 |
| 40 | 7.5 | 33.6 | 18.6 | 33.3 | 6.8 |
| 50 | 10.9 | 30.9 | 12.3 | 37.2 | 8.2 |
| 55 | 8.6 | 35.4 | 9.7 | 35.9 | 10.3 |
| 60 | 7.2 | 35.5 | 8.4 | 35.7 | 12.8 |
| 70 | 5.4 | 34.4 | 7.3 | 37.4 | 15.4 |

Reaction Conditions:

Mycelia having 5 units of fructose transferase enzyme activity per 1 g of solid sucrose were reacted with sucrose solution (pH 6.0) at various temperature conditions for 88 hours.

What we claim is:

1. A method for the production of branched fructooligosaccharides of the following formula:

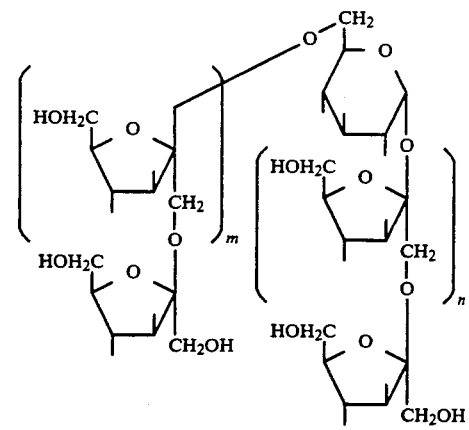

wherein $m = 0-10$, $n = 0-8$ and $m+n = 3-10$ comprising treating a sucrose solution containing at least 30% sucrose with the mycelia or the enzyme prepared from the mycelia of the microorganism *Aspergillus sydowi* at a reaction temperature in the range of 40°-60° C., subsequently removing the branched fructooligosaccharides produced, and separating said branched fructooligosaccharides from other compounds produced.

2. A method for the production of branched fructooligosaccharides according to claim 1, wherein the mycelia of *Aspergillus sydowi* are utilized.

3. A method for the production of branched fructooligosaccharides according to claim 1, wherein the enzyme from the mycelia of *Aspergillus sydowi* is utilized.

4. The method for the production of branched fructooligosaccharides as defined in claim 1 wherein said sucrose solution contains 30-80% sucrose.

5. The method for the production of branched fructooligosaccharides as defined in claim 1 wherein said sucrose solution contains 50-80% sucrose.

6. The method for the production of branched fructooligosaccharide as defined in claim 4 wherein said reaction temperature is about 40° C.

7. The method for the production of branched fructooligosaccharides as defined in claim 4 wherein said reaction temperature is about 50° C.

8. The method for the production of branched fructooligosaccharide as defined in claim 4 wherein said reaction temperature is about 55° C.

9. The method for the production of branched fructooligosaccharides as defined in claim 5 wherein said reaction temperature is about 40° C.

10. The method for the production of branched fructooligosaccharides as defined in claim 5 wherein said reaction temperature is about 50° C.

11. The method for the production of branched fructooligosaccharides as defined in claim 5 wherein said reaction temperature is about 55° C.

12. The method for the production of branched fructooligosaccharides as defined in claim 1 wherein said enzyme is present in an amount of at least 5 units per gram of solid sucrose.

* * * * *